United States Patent
Woo et al.

[11] Patent Number: 5,371,306
[45] Date of Patent: Dec. 6, 1994

[54] MODIFIED MAGNESIUM OXIDE CATALYST

[75] Inventors: Seong-Ihl Woo; Won-Choon Choi, both of Seoul; Kwang-Ho Park, Taejon; Jin-Do Kim, Seoul, all of Rep. of Korea

[73] Assignee: Korea Advanced Institute of Science and Technology and Lucky Ltd., Rep. of Korea

[21] Appl. No.: 175,297

[22] Filed: Dec. 29, 1993

[30] Foreign Application Priority Data

Dec. 31, 1992 [KR] Rep. of Korea ............ 92-27094

[51] Int. Cl.$^5$ .......... C07C 37/00; C07C 37/11; B01J 23/00; B01J 23/32
[52] U.S. Cl. .......... 568/804; 502/300; 502/324; 502/326; 502/328
[58] Field of Search .......... 502/300, 324, 326, 328, 502/323; 568/804

[56] References Cited

U.S. PATENT DOCUMENTS

| | | | |
|---|---|---|---|
| 3,280,201 | 10/1966 | Hamilton | 568/804 |
| 3,306,874 | 2/1967 | Hag | 568/804 |
| 3,446,856 | 5/1969 | Hamilton | 568/804 |
| 3,463,824 | 8/1969 | Vellian | 568/804 |
| 3,479,410 | 11/1969 | Hamilton | 568/804 |
| 3,716,589 | 2/1973 | Kotanicwara | 568/804 |
| 3,748,282 | 7/1973 | Evans | 568/804 |
| 3,751,488 | 8/1973 | Van Sorge | 568/804 |
| 3,790,641 | 2/1974 | Ushima et al. | 568/804 |
| 3,843,606 | 10/1974 | Van Sorge | 568/804 |
| 3,855,318 | 12/1974 | Nakajima et al. | 568/804 |
| 3,867,466 | 2/1975 | Endou et al. | 568/804 |
| 3,873,628 | 3/1975 | Van Sorge | 568/804 |
| 3,901,947 | 8/1975 | Enomoto et al. | 568/804 |
| 3,953,529 | 4/1976 | Vonemitsu | 568/804 |
| 3,962,126 | 6/1976 | Pecak | 568/804 |
| 3,968,172 | 7/1976 | Ichikawa | 568/804 |
| 3,971,832 | 7/1976 | Watanaba | 568/804 |
| 3,972,836 | 8/1976 | Van Doyer | 568/804 |
| 3,974,229 | 8/1976 | Van Sorg | 568/804 |
| 4,041,085 | 8/1977 | Frabetti | 568/804 |
| 4,097,411 | 6/1978 | Van Sorge | 568/804 |
| 4,227,023 | 10/1980 | Leach | 568/804 |
| 4,227,024 | 10/1980 | Leash | 568/804 |
| 4,503,272 | 3/1985 | Bennett, Jr. et al. | 568/804 |
| 4,517,389 | 5/1985 | Katsumata et al. | 568/804 |

OTHER PUBLICATIONS

S. Balsama et al., Alkylation of Phenol with Methanol Over Zeolites, Applied Catalysis, 13:161–170 (1984).

V. Venkat Rao et al., Alkylation of Phenol Over Simple Oxides and Supported Vanadium Oxides, 61:89–97 (1990).

V. Venkat Rao et al., Selective Alkylation of Phenol to 2.6-Xylenol Over Vanadia–Chromia Mixed Oxide Catalysts, Applied Catalysis, 49:165–174 (1989).

(List continued on next page.)

Primary Examiner—Werren B. Lone
Attorney, Agent, or Firm—Ostrolenk, Faber, Gerb & Soffen

[57] ABSTRACT

The present invention relates to a novel oxide catalyst, more specifically, a novel modified magnesium oxide catalyst which is highly active and selective for ortho-alkylation of phenol.

The catalysts for phenol alkylation of the invention are represented as $Mg_aMn_bL_cT_dQ_eO_x$.

wherein:
L is vanadium or chromium;
T is alkali metal, alkali earth metal, lead, bisumth, cobalt, aluminum, silicon., gallium, germanium or molybdenum;
Q is antimony, cesium or iron;
$b/a = 0$ to 0.35 (atomic molar ratio);
$c/a = 0.01$ to 0.35 (atomic molar ratio);
$d/a = 0$ to 0.35 (atomic molar ratio);
$e/c = 0.1$ to 10 (atomic molar ratio); and,
x is determined by oxidation state of each component.

8 Claims, No Drawings

OTHER PUBLICATIONS

Hideshi Hattori et al., The Differences in Surface and Catalytic Properties of Two Magnesium Oxides Prepared From the Hydroxide and the Carbonate Hydroxide, Bull. Chem. Soc. Japan, 49:969–972 (1976).

R. Pierantozzi and A. F. Nordquist, Selective O–Alkylation of Phenol with Methanol, Applied Catalysis, 21:263–271 (1986).

M. Marczewski et al., Alkylation of Aromatics Part I. Reaction Network of the Alkylation of Phenol by Methanol on Ushy Zeolite, J. Mol. Cat., 50:211–218 (1989).

Fumio Nozaki and Isao Kimura, A Study of Catalysis by Metal Phosphates. IV. The Alkylation of Phenol with Methanol Over Metal Phosphate Catalysts, Bull. Chem. Soc. Japan, 50(3):614–619 (1977).

Takeshi Kotanigawa et al., Methylation Phenol Over Metallic Oxides, Bull. Chem. Soc. Japan, 44:1961–1964 (1971).

H. Grabowska et al., Synthesis of 2,6–Xylenol by Alkylation of Phenol with Methanol. Applied catalysis, 47:351–355 (1989).

M. Marczewski et al., Alkylation of Aromatics II. Alkylation of Penol with Methanol on Various Zeolites Hetrerogeneous Catalysis and Fine Chemicals, Elsevier Science PUB.: Amsterdam 1988, 273–282.

J. M. Campelo et al., Alpo$_4$–TiO$^2$ Catalysis IV. The Alkylation of Phenol with Methanol Heterogeneous Catalysis and Fine Chemicals , Elsevier Science Pub.: Amsterdam 1988, 249–256.

P. D. Chantel et al., Reactions of Phenolic Compounds Over HZSM–5, Applied Catalysis, 18:133–145 (1985).

MODIFIED MAGNESIUM OXIDE CATALYST

FIELD OF THE INVENTION

The present invention relates to a novel oxide catalyst, more specifically, a novel modified magnesium oxide catalyst which is highly active and selective for ortho-alkylation of phenol.

BACKGROUND OF THE INVENTION

Phenol alkylation has been focused on industrial application including the engineering plastic areas, grounded on its production of 2,6-xylenol, a monomer of a good heat-resisting poly-(2,6-dimethyl)phenylene oxide resin; however, catalysts employed in the reaction have not been commercially available owing to their short life time and low activity.

In this connection, studies on the develoment of highly active and selective phenol alkylating catalysts have been actively carried out; and the following catalysts have been suggested: U.S. Pat. No. 3,446,856 discloses MgO catalyst which is highly selective for ortho-alkylation of phenol at the temperature range of 475° to 600° C. and produces little byproducts by reducing contact time with its product, i.e., 2,6-xylenol. However, said catalyst can not be commercialized due to its low activity.

Ger. Offen 1248666 teaches phenol alkylating reaction employing aluminum catalyst; said catalyst, however, has not been applied in a practical manner, owing to its low selectivity and unstability.

On the other hand, M. Inoue et al teaches that activity of catalyst comprising metal oxides such as ZnO, $Fe_2O_3$, $Cr_2O_3$, $TiO_2$ and $Al_2O_3$ is increased in proportion to the temperature elevation in the aqueous-phase alkylation reaction[see: M. Inoue and S. Enomoto, Chem. Pharm. Bull., 24:2199 (1976)]. In the case of this catalyst, selectivity for alkylation at the ortho-position, however, is abruptly decreased at the temperature over 400° C.

F. Nozaki et al reported that they had carried out vapor-phase phenol alkylating reaction employing $Ca_3(PO_4)_2$ under atmospheric pressure at 350° C. and 500° C., where 77.7% of conversion and 88% selectivity for ortho-position methylation were obtained at the initial state and most of reactants were converted to o-cresol and 2,6-xylenol with the lapse of time.

Some other literature discloses that activities and selectivities of catalysts employed to the phenol alkylation reaction are sensitively changed according to their own acidity and basicity, and their properties can be changed by employing zeolite and mixed metal oxides. However, most of prior art catalysts have not been practically applied to industrial scale owing to their low activity, selectivity and short life time.

Accordingly, a need for the development of a highly active and selective catalyst in the vapor-phase ortho-alkylation of phenol has continued in the art.

SUMMARY OF THE INVENTION

In accordance with the present invention, it has been discovered that a mixed metal oxide catalyst composition comprising magnesium oxide has a superior catalytic effect to any other prior art metal oxide catalyst in light of activity, selectivity and contol of acidity and basicity.

A primary object of the present invention is, therefore, to provide a novel mixed metal oxide catalyst for ortho-alkylation of phenol with high activity, selectivity and longer life time.

Another object of the present invention is to provide a novel proces for preparing said catlyst by employing precipitation and doping methods.

DETAILED DESCRIPTION OF THE INVENTION

Catalysts of the invention are prepared by the process employing a precipitation method or doping method.

Mixed metal oxide catalysts of the invention are prepared as follows: to an aqueous solution are added metal compound component and $Mg(NO_3)_2$, and the resulting solution is dissolved completely under vigorous stirring. Then, the resultant thus obtained is dried under heating to evaporate water to produce mixed oxide catalyst of tile invention. In accordance with the process employing said precipitation method, catalysts such as Cr—MgO, Fe—MgO, Al—MgO, Ce—MgO, Mn—MgO and Co—MgO are prepared.

On the other hand, metal-doped catalysts of the invention are prepared as follows: basic magnesium carbonate (hereinafter referred to as "BMC") is dispersed in distilled water, and to the resultant are added metal components in a dropwise to dope and then dried in the rotavapor to produce catalysts of the invention. In accordance with the process employing the dopping method, catalysts such as V—Mn—MgO, Na—V—Mn—MgO, Li—V—Mn—Mgo, K—V—MgO, Rb—V—Mn—MgO, Cs—V—Mn—MgO, Ce—V—Mn—Mgo, Ce—V—Mn—MgO—$Sb_2O_3$ and Na—Mn—MgO are prepared.

Magnesium oxide catalysts for phenol alkylation of the invention comprise:

(1) magnesium, vanadium and manganese, preferably 0.1 to 35 mol % vanadium and 0 to 35 mol % manganese, based on moles of magnesium;.

(2) magnesium, chromium and manganese, preferably 0.1 to 35 mol % chromium and 0 to 35 mol % manganese, or further, 0.1 to 35 mol % at least one metal selected from the group consisting of alkaline metal, alkaline earth metal, lead, cerium, bismuth, cobalt, aluminum, silicon, gallium, germanium, iron and antimony, based on moles of magnesium;

(3) magnesium, 0 to 35 mol % manganese and 0.1 to 35 mol % at least one metal selected from the group consisting of alkali metal, alkaline earth metal, cerium, bismuth, cobalt, aluminum, gallium, germanium, iron and antimony, based on moles of magnesium; and, (4) magnesium, and Mg/Metal = 1 to 10 (molar ratio) of least one metal selected from the group consisting of iron, cobalt, aluminum and cerium.

The catalysts for phenol alkylation of the invention are represented as $Mg_aMn_bL_cT_dQ_eO_x$.

wherein:

L is vanadium or chromium;

T is alkaline metal, alkaline earth metal, lead, bisumth, cobalt, aluminum, silicon, gallium, germanium or molybdenum;

Q is antimony, cesium or iron;

b/a = 0 to 0.35 (atomic molar ratio);

c/a = 0.01 to 0.35 (atomic molar ratio);

d/a = 0 to 0.35 (atomic molar ratio);

e/c = 0.1 to 10 (atomic molar ratio); and, x is determined by oxidation state of each component.

The catalysts of the invention have advantages over prior art materials as follows: the catalysts of the invention maintain a long life time of high activity after initial 2 hours, while the prior art catalysts bring about rapid inactivation, grounded on an unbalance of acidity and basicity. Further, the selectivity for o-cresol and 2,6-xylenol of the present catalysts is over 90%, so that high yield of 2,6-xylenol can be obtained by continuous reaction of recycling o-cresol. Moreover, the catalysts of the invention produce only o-cresol and 2,6-xylenol without producing byproducts; and therefore, process for separating products is economical in light of its simplicity.

The present invention is further illustrated in the following examples, which should not be taken to limit the scope of the invention.

EXAMPLE 1

A magnesium oxide catalyst was prepared by the process employing precipitation method. A mixture of magnesium nitrate and aluminum nitrate with a molar ratio of 1:1 (Mg/Al=1) was dissolved in distilled water and subsequently precipitated by the addition of ammonia water. Then, the distilled water was evaporated from the precipitate by heating with continuous stirring, and the resultant was dried at 120° C. for 24 hours and calcined at the air stream of 500° C. to produce catalyst of the invention. The reactants coming from the preheated vaporizer was fed to reactor for phenol alkylation; and reaction conditions and results were summarized in Table 1.

TABLE 1

| condition of reaction | |
|---|---|
| methanol/phenol | 5 (molar ratio) |
| temperature of reaction | 460° C. |
| WHSV (1/g)* | 3.12 |
| results of reaction | |
| conversion of phenol | 73.2% |
| selectivity for o-cresol | 46.4% |
| selectivity for 2,6-xylenol | 40.0% |
| selectivity for 2,4- or 2,5-xylenol | 10.4% |

*WHSV: Weight Hourly Space Velocity

As clearly illustrated in Table 1, phenol was alkylated primarily at ortho-position; and, o-cresol could be recycled and reacted with unreacted phenol to afford high yield of 2,6-xylenol.

EXAMPLE 2

Mixed metal oxide catalysts were prepared analogously in Example 1, except for employing cesium nitrate, manganese nitrate and ferric nitrate in stead of aluminum nitrate; and the results of reaction were shown in Table 2.

TABLE 2

| catalyst | conversion of phenol (%) | selectivity (%) | | |
|---|---|---|---|---|
| | | o-cresol | 2,6-xylenol | 2,4- or 2,5-xylenol |
| Ce—MgO | 46.1 | 70.3 | 29.7 | 0.0 |
| Mn—MgO | 75.9 | 61.4 | 38.6 | 0.0 |
| Fe—MgO | 38.7 | 69.1 | 20.9 | 0.0 |

From the Examples 1 and 2, the average of life time of the employed catalysts was determined to be about 4,000 hours and it was also determined that the longer the contact time of phenol with catalyst was, the higher the selectivity for 2,6-xylenol and conversion of phenol.

EXAMPLE 3

A magnesium oxide catalyst was prepared by the process employing the doping method. To distilled water containing 6 g of BMC were added 0.073 g of $NH_4VO_3$ and 0.179 g of manganese nitrate. Then, distilled water was evaporated in a rotatory evaporator and the resultant thus obtained was dried over a heating drier of 120° C. and calcined under the oxygen environment of 500° C. The other conditions of reaction were employed in a similar manner to tile Example 1. The results of reaction employing the catalyst prepared as above were as followings: conversion of phenol was 70.5% and the selectivity for o-cresol, 2,6-xylenol, 2,4- or 2,5-xylenol and 2,4,6-xylenol were 57.2%, 37.4% 3.1% and 2.3% respectively

EXAMPLE 4

In a manner analogous to the process described in Example 3, except for employing 0.146 g of $NH_4VO_3$. Results of the reaction were as followings: conversion of phenol was 91.7% and the selectivity for o-cresol, 2,6-xylenol, 2,4- or 2,5-xylenol and 2,4,6-xylenol were determined to be 30.1%, 47.6%, 5.6% and 16.7%, respectively.

EXAMPLE 5

The catalyst prepared in Example 4 was mixed with alkali metal and alkali earth metal compounds to produce more active catalysts: 6 g of BMC was dispersed in distilled water and to the resulting solution was added 0.173 g of manganese nitrate and 0.151 g of $MH_4VO_3$. Then, alkaline metal (Li nitrate 0.044 g, K nitrate 0.055 g, Rb nitrate 0.095 g, Cs nitrate 0.125 g) and alkal earth metal (Ca nitrate 0.072 g, Sr nitrate 0.115 g, Ba nitrate 0.142 g) or proper combination of the above metals were mixed with the said composition. The other process for preparing catalysts was the same as Example 3; and results of reaction employing catalysts prepared as above, were shown in Table 3.

TABLE 3

| catalyst | conversion of phenol (%) | selectivity (%) | | | |
|---|---|---|---|---|---|
| | | o-cresol | 2,6-xylenol | 2,4- or 2,5-xylenol | 2,4,6-xylenol |
| Li—V—Mn—MgO | 59.8 | 60.1 | 38.1 | 1.0 | 0.8 |
| Na—V—Mn—MgO | 78.3 | 45.3 | 48.5 | 3.9 | 2.2 |
| K—V—Mn—MgO | 69.1 | 52.9 | 38.8 | 4.9 | 3.3 |
| Rb—V—Mn—MgO | 42.6 | 61.3 | 35.8 | 3.0 | 0.0 |
| Cs—V—Mn—MgO | 64.2 | 62.1 | 33.2 | 4.0 | 0.7 |
| Ca—V—Mn—MgO | 52.4 | 60.2 | 37.2 | 2.1 | 0.5 |
| Sr—V—Mn—MgO | 70.1 | 45.1 | 51.7 | 1.1 | 2.1 |
| Ba—V—Mn—MgO | 41.9 | 62.1 | 31.8 | 2.8 | 3.3 |

EXAMPLE 6

Oxide catalysts were prepared by the process employing the doping method, based on mixed metal oxides containing antimony trioxide, vanadium and manganese: 8 to 12 g of ammonium vanadate or manganese nitrate was mixed with 10 to 14 g of antimony trioxide in 300 ml of distilled water with stirring for 24 hours. Then, distilled water was evaporated from the solution thus obtained under heating with continuous stirring, and the resultant was dried for 24 hours in a drying oven of 120° C. and calcined in the air stream of 520° C. for 6 hours. The other process for preparing catalysts was the same as Example 3; and results of reaction employing Ce, Fe and Pb as well as Sb were shown in Table 4.

TABLE 4

| catalyst | conversion of phenol (%) | selectivity (%) | | | |
|---|---|---|---|---|---|
| | | o-cresol | 2,6-xylenol | 2,4- or 2,5-xylenol | 2,4,6-xylenol |
| Sb V Ox—Sb Mn—Ox—MgO | 89.9 | 32.8 | 62.5 | 0.5 | 4.3 |
| Ce V Ox—Ce Mn—Ox—MgO | 72.8 | 42.9 | 52.5 | 3.5 | 0.3 |
| Fe V Ox—Fe Mn—Ox—MgO | 90.1 | 31.8 | 58.6 | 2.5 | 2.3 |
| Pb V Ox—Pb Mn—Ox—MgO | 83.9 | 48.2 | 48.9 | 0.8 | 0.1 |

EXAMPLE 7

To the catalyst prepared in Example 4 were added Fe, Bi, Co, Pb, Al, Si, Ga, Ge; and Cr instead of V in Example 4 was mixed with the resultant thus obtained to provide a highly active catalyst: i.e., 6 g of BMC was dispersed in distilled water and 0.173 g of manganese nitrate and 0.243 g of chromium nitrate were added to the resulting solution. Then, metal oxides (Fe nitrate 0.121 g, Al nitrate 0.121, Si oxide 0.166 g, Ga nitrate 0.121 g, Ge nitrate 0.155 g) or proper combination of the aboves were mixed with the said composition. The other process of preparing catalysts was the same as Example 3; and results of reaction employing the catalysts thus prepared were shown in Table 5.

TABLE 5

| catalyst | conversion of phenol (%) | selectivity (%) | | | |
|---|---|---|---|---|---|
| | | o-cresol | 2,6-xylenol | 2,4- or 2,5-xylenol | 2,4,6-xylenol |
| Fe—Cr—Mn—MgO | 68.1 | 70.9 | 28.1 | 1.0 | 0.0 |
| Bi—Cr—Mn—MgO | 77.3 | 55.8 | 34.9 | 5.2 | 3.8 |
| Co—Cr—Mn—MgO | 50.1 | 66.3 | 28.9 | 1.9 | 2.9 |
| Pb—Cr—Mn—MgO | 66.2 | 58.3 | 40.1 | 1.0 | 0.6 |
| Al—Cr—Mn—MgO | 76.4 | 38.1 | 60.0 | 1.9 | 0.0 |
| Si—Cr—Mn—MgO | 80.2 | 35.1 | 60.1 | 4.0 | 0.8 |
| Ga—Cr—Mn—MgO | 88.9 | 30.2 | 63.5 | 5.2 | 1.0 |
| Ge—Cr—Mn—MgO | 87.1 | 36.4 | 56.3 | 4.8 | 1.9 |

EXAMPLE 8

The degree of inactivation of the catalysts of the invention were determined by the known method in the art. As can be seen in Table 6, it is clear that the catalysts of the invention have long life times and high activity and selectivity as well.

TABLE 6

| catalyst | degree of inactivation (%) |
|---|---|
| Na—Mn—MgO | 8 |
| Na—V—Mn—MgO | 10 |
| Cs—V—Mn—MgO | 7 |
| Rb—V—Mn—MgO | 9 |
| Ba—V—Mn—Mgo | 11 |
| Sb V Ox—Sb Mn Ox—MgO | 5 |
| Ce—MgO | 5 |
| Fe—MgO | 6 |
| Ge—Cr—Mn—MgO | 13 |

What is claimed is:

1. A magnesium oxide catalyst for phenol alkylation comprising magnesium, vanadium and manganese.

2. The magnesium oxide catalyst of claim 1, wherein it comprises 0.1 to 35 mol % of vanadium and 0 to 35 mol % of manganese, based on moles of magnesium.

3. A magnesium oxide catalyst for phenol alkylation comprising magnesium, chromium and manganese.

4. The magnesium oxide catalyst of claim 3, wherein it comprises 0.1 to 35 mol % of chromium and 0 to 35 mol % manganese, based on moles of magnesium.

5. The magnesium oxide catalyst of claim 3, wherein it further comprises 0.1 to 35 mol % of at least one metal selected from the group consisting of alkaline metal, alkaline earth metal, lead, cerium, bismuth, cobalt, aluminum, silicon, gallium, germanium, iron and antimony, based on moles of magnesium.

6. A magnesium oxide catalyst for phenol alkylation comprising magnesium, 0 to 35 mol % of manganese and 0.1 to 35 mol % of at least one metal selected from the group consisting of alkaline metal, alkali earth metal, cerium, bismuth, cobalt, aluminum, gallium, germanium, iron and antimony, based on moles of magnesium.

7. A magnesium oxide catalyst for phenol alkylation comprising magnesium, and 1 to 10 molar ratio of Mg/Metal of at least one metal selected from the group consisting of iron, cobalt, aluminum and cerium.

8. A magnesium oxide catalyst composition for phenol alkylation represented as:

$$Mg_aMn_bL_cT_dQ_eO_x$$

wherein:

L is vanadium, chromium;
T is alkali metal, alkaline earth metal, lead, bismuth, cobalt, aluminum, silicon, gallium, germanium or molybdenum;
Q is antimony, cesium or iron;
b/a is 0 to 0.35(atomic molar ratio);
c/a is 0.01 to 0.35(atomic molar ratio);
d/a is 0 to 0.35(atomic molar ratio);
e/c is 0.1 to 10(atomic molar ratio); and,
x is determined by oxidation state of each component.

* * * * *